United States Patent
McAdams

(10) Patent No.: US 8,895,773 B2
(45) Date of Patent: Nov. 25, 2014

(54) MANUFACTURE AND USE OF ALKYL P-TOLUATES

(75) Inventor: Carina Araullo McAdams, Wilmington, NC (US)

(73) Assignee: Invista North America S.a.r.l., Wilmington, DE (US)

( * ) Notice: Subject to any disclaimer, the term of this patent is extended or adjusted under 35 U.S.C. 154(b) by 225 days.

(21) Appl. No.: 12/463,018

(22) Filed: May 8, 2009

(65) Prior Publication Data

US 2009/0286912 A1    Nov. 19, 2009

Related U.S. Application Data

(60) Provisional application No. 61/051,806, filed on May 9, 2008.

(51) Int. Cl.
| | |
|---|---|
| *C07C 67/03* | (2006.01) |
| *C07C 69/76* | (2006.01) |
| *C08K 5/101* | (2006.01) |
| *C08K 5/10* | (2006.01) |

(52) U.S. Cl.
CPC . *C08K 5/10* (2013.01); *C07C 69/76* (2013.01); *C08K 5/101* (2013.01); *C07C 67/03* (2013.01)
USPC ........... 560/103; 560/114; 524/292; 524/318; 524/569

(58) Field of Classification Search
CPC ......... C07C 67/03; C07C 69/76; C08K 5/101
USPC ................... 524/292, 318, 569; 560/103, 114
See application file for complete search history.

(56) References Cited

U.S. PATENT DOCUMENTS

| | | | |
|---|---|---|---|
| 3,376,246 A | * | 4/1968 | Valentine et al. ............. 524/294 |
| 3,635,856 A | * | 1/1972 | Kaneko et al. .................. 524/57 |
| 4,010,195 A | | 3/1977 | Isogai et al. |
| 4,112,240 A | * | 9/1978 | Hulsmann et al. ............. 560/112 |
| 4,273,696 A | * | 6/1981 | Marshall et al. ............... 524/290 |
| 4,371,654 A | * | 2/1983 | Spielau et al. ................. 524/296 |

FOREIGN PATENT DOCUMENTS

| | | | |
|---|---|---|---|
| CN | 1199042 | | 11/1998 |
| DE | 3839418 | * | 6/1989 |
| DE | 3989418 | * | 6/1989 |
| WO | 2004/104079 | | 12/2004 |
| WO | WO2004/104079 | | 12/2004 |

OTHER PUBLICATIONS

Synthesis 2006, No. 14, pp. 2392-2396, D. Subhas Bose et al., A Facile, Catalytic and Environmentally Benign Method for Esterification of Carboxylic Acids and . . . .
J. Am. Chem. Soc. 2008, vol. 130, No. 10, pp. 2944-2945, Takashi Ohshima et al., Enzyme-Like Chemoselective Acylation of Alcohols in the Presence of Amines Catalyzed . . . .
J. Org. Chem. 1997, vol. 62, No. 23, pp. 8240-8242, Matthew G. Stanton et al., "A Mild Protocol for the Conversion of Simple Esters to tert-Butyl Esters".
Tetrahedron Letters 2006, 47, pp. 565-567, Apurba Bhattacharya et al., Surfactant-mediated solvent-free dealkylative cleavage of ethers and esters and trans-alkylation . . . .

* cited by examiner

*Primary Examiner* — Tae H Yoon
(74) *Attorney, Agent, or Firm* — Womble Carlyle Sandridge & Rice, LLP

(57) ABSTRACT

The present invention relates to the manufacture of alkyl p-toluates from an alkyl p-toluic acid ester and a monofunctional, branched, linear or cyclic medium chain length alkyl alcohol, and their use as a plasticizer in polymers. Additionally, the present invention relates to articles and materials comprising such alkyl p-toluates.

10 Claims, No Drawings

MANUFACTURE AND USE OF ALKYL P-TOLUATES

FIELD OF THE INVENTION

The present invention relates to the manufacture of alkyl p-toluates from an alkyl p-toluic acid ester and a mono-functional, branched, linear or cyclic medium chain length alkyl alcohol, and their use as a plasticizer in polymers. Additionally, the present invention relates to articles and materials comprising such alkyl p-toluates.

BACKGROUND OF THE INVENTION

A major use of plasticizers is in the polymer industry, for example in the polyvinyl chloride (PVC) industry. Without the availability of low cost plasticizers PVC would have little value. The plasticizers impart flexibility to the PVC. The family of phthalate esters is the predominant plasticizer used in PVC. Options to using these phthalate esters have been explored.

For example, CN-A-1199042 describes the manufacture and use of long chain alkyl benzoates as plasticizers. The starting material for the manufacture of the benzoates is methyl benzoate-rich ester mixture which is obtained from a byproduct stream of a dimethyl terephthalate (DMT) production line, and contains over 80 weight % of methyl benzoate and a low weight percentage of methyl p-toluate (MpT). Additionally, WO-A-2004/104079 describes the conversion of MpT with diols to form diesters, which are used as plasticizers.

Increasing environmental and toxicological concerns associated with phthalate esters has lead to the need to develop alternative low cost ester plasticizers that function at least equally as well as compared to phthalate esters.

SUMMARY OF THE INVENTION

In accordance with the present invention, it has now been found that certain alkyl p-toluates can be manufactured at a low cost and used as plasticizers in polymers. These alkyl p-toluates function equal to or better than phthalic esters when used in PVC. The present invention substitutes a low cost acid for the phthalic acid used in the phthalate esters. The present invention relates to a method for the manufacture of an alkyl p-toluate of formula I,

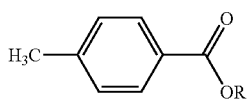
(I)

wherein R is a $C_4$-$C_{20}$ branched, linear or cyclic alkyl radical, comprising:
transesterifying an ester comprising at least about 80% by weight of $C_1$-$C_4$ alkyl p-toluic acid ester and one or more $C_4$-$C_{20}$ mono-functional branched, linear or cyclic aliphatic alcohol. Additionally, the present invention relates to a composition comprising a polymer and one or more alkyl p-toluates of formula I as above, as well as articles and materials comprising the composition produced by processes of the present invention.

DETAILED DESCRIPTION OF THE INVENTION

The present invention can be characterized by a method for the manufacture of an alkyl p-toluate of formula I,

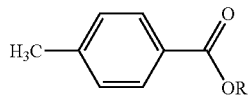
(I)

wherein R is a $C_4$-$C_{20}$ branched, linear or cyclic alkyl radical, comprising:
transesterifying an ester comprising at least about 80% by weight of $C_1$-$C_4$ alkyl p-toluic acid ester and one or more $C_4$-$C_{20}$ mono-functional branched, linear or cyclic aliphatic alcohol. The alkyl p-toluic acid ester can be methyl p-toluate. Additionally, the present invention relates to a composition comprising a polymer and one or more alkyl p-toluates of formula I as above, as well as articles and materials comprising a composition produced by processes of the present invention.

Dimethyl terephthalate (DMT) is typically produced on an industrial scale by the oxidation of p-xylene via the Witten process and modifications thereof. After the first oxidation process a stream that is rich in methyl p-toluate (MpT) is produced that is normally separated from the crude DMT and recycled for further oxidation. According to the present invention this stream of crude MpT can be isolated and used as the raw material for the preparation of medium chain length alkyl p-toluates. Crude MpT can be removed from the DMT production process in large amounts (e.g. 25-35 wt.-%) without negatively impacting the DMT production process itself. This crude MpT can then be used as a feedstock for the synthesis of medium chain length allyl p-toluates by transesterification with mono-functional, branched, linear or cyclic medium chain length ($C_4$-$C_{20}$) alkyl alcohols. The transesterification can be in the presence of a suitable catalyst. These medium chain length alkyl p-toluates have been found to provide an equal to or higher plasticizer efficiency than phthalate esters in PVC.

Depending on the basic oxidation process the isolated crude MpT contains varying amounts of byproducts. A crude MpT stream which can be used in the present invention typically comprises at least about 80% by weight of MpT, for example at least about 85% by weight or at least about 90% by weight (based on the weight of the crude MpT). Typical major byproducts are benzoic acid methyl ester (BME), terephthalic aldehyde methyl ester (TAME) and DMT. The total amount of byproducts in the crude MpT which can be used in the present invention typically amounts to no more than about 20% by weight, for example no more than about 15% by weight or no more than about 10% by weight (based on the weight of the crude MpT). The amount of benzoic acid methyl ester in this crude MpT stream which can be used in the present invention is less than about 15% by weight, for example less than about 10% by weight or less than about 5% by weight (based on the weight of the crude MpT).

Through further purification of the crude MpT, e.g. by distillation, the amount of MpT can be further increased and, thus, the amount of byproducts can be further decreased. Grades with amounts of MpT of greater than about 99% by weight, for example greater than about 99.5% by weight (based on the weight of the crude ester) can be achieved and used in the present invention.

Crude or purified MpT can be converted with corresponding alkyl alcohols in a transesterification reaction, optionally in the presence of a suitable catalyst, to the alkyl p-toluates with small amounts of byproducts according to the invention.

The methanol produced in this transesterification reaction can be distilled off from the reaction mixture in order to shift the reaction equilibrium towards the alkyl p-toluates.

Suitable alkyl alcohols for the transesterification reaction are mono-functional branched, linear, or cyclic alcohols with 4 to 20 carbon atoms, for example 8 to 16 carbon atoms or 8 to 13 carbon atoms. The allyl alcohol can be primary alcohols. One, two or more of these alcohols can be used in the transesterification reaction. If mixtures of two or more alcohols are co-reacted these can be added in equimolar or different molar amounts. In general the alcohols or mixture of alcohols can be employed stoichiometrically, sub-stoichiometrically or in excess. It is suitable to use the component with the lower boiling point in excess in order to ensure complete conversion of the higher boiling component and additionally facilitate the removal of the methanol from the reaction mixture.

Suitable branched primary alkyl alcohols for use in the present invention can be: 2-ethylhexanol, isononanol, isomers of propylheptanol (for example 2-propylheptanol, 4-methyl-2-propylhexanol, 5-methyl-2-propylhexanol), isodecanol, isoundecanol and isotridecanol. The iso-alcohols are mixtures of different primary saturated alcohols with different length and varying degree of branching depending on the catalyst system used in their synthesis and the fraction of distillation. The different compositions of isononyl alcohol, for example are referenced by different CAS numbers (e.g. 27458-94-2, 68515-81-1, 68526-84-1). Suitable linear alkyl alcohols can be 1-butanol, 1-pentanol, 1-hexanol, 1-heptanol, 1-octanol, 1-nonanol, 1-decanol, 1-undecanol and their lower or higher homologues and mixtures thereof. Suitable cycloalkyl alcohols can be cyclododecanol and cyclohexanol.

Suitable reaction temperatures for the transesterification reaction can be in the range of from about 160° C. to about 260° C., for example in the range of from about 180° C. to about 240° C. The optimum temperature depends on the materials used, the catalyst type, concentrations and the desired progress of the reaction. In addition the reaction can be performed under reduced pressure (for example less than about 1000 mbar) in case of high boiling alcohols or under overpressure (for example greater than about 1000 mbar) for low boiling alcohols.

A catalyst can be added to the transesterification reaction to facilitate the reaction. A suitable catalyst for this type of reaction can be a titanium compound, a zinc compound, an aluminum compound, a cobalt compound, a manganese compound, a tin compound or mixtures thereof; for example organic alkoxy titanates such as tetra-butyl titanate (TBT) and tetra-isopropyl titanate (TPT), zinc acetate, aluminum triisopropylate, cobalt acetate, manganese acetate or mono-butyl tin oxalate. The catalyst concentration depends on the type of catalyst and can be in the range of from about 0.001 to about 1.0 weight %, for example in the range of from about 0.005 to about 0.5 weight % (based on the weight of MpT).

The transesterification product can be purified by distillation, for example under reduced pressure (vacuum distillation). Unreacted starting materials (e.g. MpT and/or alcohol) can be distilled off in a first step under reduced pressure (for example in the range of from about 0.1 to about 100 mbar). During a second distillation step, the temperature can be increased for the distillation of the alkyl p-toluates; the reduced pressure can be held at the same level, but optionally the pressure can be further reduced. A wiped wall evaporator can be used for either or both of these purification steps.

Where crude MpT is used as a starting material the side components are also transesterified resulting in corresponding medium chain length alkyl benzoates, medium chain length dialkyl terephthalates and terephthalic aldehyde medium chain length alkyl esters as the byproducts in the medium chain length alkyl p-toluate. While dialkyl terephthalate and terephthalic aldehyde alkyl ester remain in the bottom of the distillation column, the alkyl benzoate is distilled in association with the main alkyl p-toluate product. Depending on the separation performance of the distillation column, the alkyl benzoate may more or less be removed from the alkyl p-toluate fraction. Typically the content of alkyl benzoate in the final product is less than about 15% by weight, for example less than about 10% by weight or less than about 5% by weight (based on the mixture of esters).

Optionally the crude transesterification product can be further purified by any other suitable purification method known to those skilled in the art, e.g. filtration over suitable media, steam distillation, treatment with activated carbon, etc.

Another embodiment of the present invention is a method for the manufacture of an alkyl p-toluate of formula I,

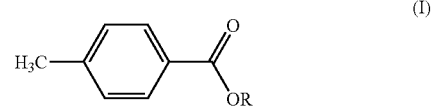

(I)

wherein R is a $C_4$-$C_{20}$ branched, linear or cyclic allyl radical, comprising:
  a. transesterifying a methyl p-toluate with one or more $C_4$-$C_{20}$ mono-functional branched, linear or cyclic aliphatic alcohol in the presence of a catalyst to form a resultant product,
  b. distilling the resultant product under vacuum to remove the unreacted methyl p-toluate and alcohol,
  c. optionally raising the temperature,
  d. optionally reducing the pressure, and
  e. distilling off the alkyl p-toluate.

Another embodiment of the present invention is a method for the manufacture of an alkyl p-toluate of formula I,

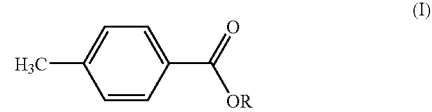

(I)

wherein R is a $C_4$-$C_{20}$ branched, linear or cyclic alkyl radical, comprising:
  a. transesterifying a methyl p-toluate with one or more $C_4$-$C_{20}$ mono-functional branched, linear or cyclic aliphatic alcohol in the presence of a catalyst to form a resultant product,
  b. distilling the resultant product under vacuum to remove the unreacted methyl p-toluate and alcohol to form a purified alkyl p-toluate,
  c. filtering the purified alkyl p-toluate, and
  d. optionally distilling the purified alkyl p-toluate under vacuum to distill off the alkyl p-toluate.

For all of the embodiments described above, the resulting final product has APHA color numbers less than about 50 Pt—Co units, for example less than or equal to about 30 Pt—Co units or less than or equal to about 20 Pt—Co units.

Melting points of the purified branched, linear or cyclic medium chain length alkyl p-toluates can be below −45° C. Optionally, any hydrolysis products formed during the transesterification reaction, such as p-toluic acid, can be neutralized prior to distillation to reduce the acid number of the ester.

Alkyl p-toluates of the present invention can be used as a plasticizer for polymers or polymer blends. The polymers or polymer blends can be homopolymer or copolymer of vinyl chloride, polyvinyl bromide, homopolymer or copolymer of ethylene, polypropylene, polybutadiene, polyvinyl acetate-derivative, polyacrylate-derivative, polymethacrylate-derivative, polystyrene-derivative or polyacrylonitrile-derivative. Suitably the polymer can be a homopolymer of vinyl chloride (PVC) or a copolymer of vinyl chloride. The PVC can be of any type selected from suspension-, mass-, micro suspension- or emulsion-PVC and mixtures thereof.

The alkyl p-toluates can be added alone or together with other plasticizers into a polymer, for example PVC or copolymers of PVC. The medium chain length alkyl p-toluates can be present in the polymer composition in a concentration of from about 1% to about 90% by weight, for example from about 15% to about 60% by weight or from about 20 and 50% by weight (based on the weight of the polymer).

The composition can contain one or more stabilizers such as metal soaps, organic phosphates, epoxy compounds, tin stabilizers and mixtures thereof. The stabilizers can provide protection against polymer degradation.

Additionally, the composition may contain further additives such as antistatic agents, antifogging additives, bio-stabilizers, fillers, UV stabilizers, anti oxidants, light stabilizers, optical brighteners, flame retardants, pigments and mixtures thereof.

For decades PVC has been used for the production of soft, flexible and rigid molded and plastisol-processed articles and belongs to the commercially most important polymers. For the production of soft PVC it is necessary to add plasticizers to the PVC. Typical plasticizers are phthalic acid diesters, in particular di-2-ethylhexyl phthalate (DEHP), diisononyl phthalate (DINP) and diisodecyl phthalate (DIDP). A major disadvantage with these plasticizers is that the processing temperature of the PVC rises with increasing chain length and can only be reduced through addition of so called fast acting gelling agents ("fast fusers") such as dibutyl phthalate (DBP) or butyl benzyl phthalate (BBP).

In PVC-plastisols the use of these fast fusers often leads to a strong increase of viscosity with time due to their high solvation force which has to be compensated by the addition of additional viscosity reducing agent.

Requirements for PVC-plastisols typically comprise a low viscosity, a low gelation (fusion) temperature and a high shelf life, i.e. a low increase of plastisol viscosity with time.

The alkyl p-toluates of the present invention, when added to PVC as plasticizer, have equal or higher plasticizer efficiency than the phthalate esters and fuse the PVC without additional gelling agents. Compared to the known plasticizers the alkyl p-toluates provide similar or even improved plasticization properties and can be produced from lower cost raw materials.

When used in plastisols the alkyl p-toluates of the present invention show beneficial properties like a low plastisol viscosity, a low increase of plastisol viscosity and a low fusion temperature.

The alkyl p-toluates of the present invention show a lower volatility than the alkyl benzoates such as those described in CN-A-1199042. The lower volatility of the alkyl p-toluates results in a higher permanence compared to the alkyl benzoates which is reflected in a lower increase of the elastic modulus of flexible PVC compounds plasticized with alkyl-p-toluates upon aging at elevated temperature. The alkyl p-toluates of the present invention therefore show a superior performance in flexible PVC compositions that are less prone to weathering than PVC compounds plasticized with alkyl benzoates. Besides the improved performance this offers economic and ecologic advantages in production as well as for the final product as less plasticizer has to be added to compensate for losses when alkyl p-toluates of the present invention are used instead of alkyl benzoates.

The alkyl p-toluates according to this invention can be used as plasticizer for the manufacture of polymer articles, for example PVC products, that are flexible at low temperatures, which are suitable for the manufacture of self adhesive films, automotive films, furniture- and office supply films, agricultural films, food films (cling film), roofing membranes, water reservoir liners, liners for swimming pools, films for preservation of structures, rain coats, shower curtains, rubber dinghies, water wings.

The alkyl p-toluates according to this invention can be used as plasticizer for the manufacture of polymer articles, for example PVC products, that are stable at high temperatures for use in the manufacture of cables, e.g. for installation, computer cables or automotive cables.

The alkyl p-toluates according to this invention can be used for the manufacture of plasticized coatings, e.g. artificial leather, tarpaulins for trucks and tents, vinyl wall coatings, conveyor belts, protective clothing and car undercoat protection.

The alkyl p-toluates according to this invention are suitable for the manufacture of plasticized flooring, e.g. vinyl cushions, compact flooring and back layer coatings of carpets.

The alkyl p-toluates according to this invention are also suitable for the manufacture of plasticized molded articles, e.g. industrial and home hoses, gaskets and seals; and shaped articles, e.g. shoes, toys, gloves and mold forms.

These articles can be manufactured by methods such as calendering, extrusion, coating, casting, dip molding, rotational molding or injection molding.

Additionally, alkyl p-toluates manufactured by the methods of the present invention can be used as a non-plasticizer component in many products. For example alkyl p-toluates can be used in paints, coatings, varnishes, adhesives, and adhesive components, sealing compounds such as caulk, surfactants, detergents, emulsifiers and lubricants.

The following examples serve to illustrate the present invention without limiting the range of applications that are arising from the description and the patent claims.

Measurement Methods

1. Color measurement—The color of the distilled final products is determined according to ISO 6271-1, which describes a visual method for estimating the color of clear liquids, in Pt—Co units, APHA color, or Gardner color.
2. Viscosity of pure plasticizers is measured with a rheometer (Rheostress RS 150 (Haake GmbH) using Thermo-Haake Rheowin Pro 2.96 software). A cone-plate system is used (plate 35 mm, cone 35 mm/1°, gap width 0.054 mm, rotating). The measurement comprises four isothermal (20° C.) segments:
    a. with linear shear stress (0.10 to 100 Pa; 120 s measuring time),
    b. with linear shear rate (0.10 to 130 s$^{-1}$; measuring time 240 s),
    c. with static shear rate (130 s$^{-1}$, measuring time 180 s)
    d. with linear shear rate (130 to 0.10 s$^{-1}$; measuring time 240 s).

The viscosity of the pure plasticizer was determined from segment c.
3. Viscosity of plastisols is measured with a rheometer (Rheostress RS 150 (Haake GmbH) using Thermo-Haake Rheowin Pro 2.96 software). A cone-plate system was used (plate 35 mm, cone 35 mm/2°, gap width 0.105 mm, rotating). The measurement comprises four isothermal (20° C.) segments:
  a. with linear shear stress (0.10 to 100 Pa; 120 s measuring time),
  b. with linear shear rate (0.10 to 130 s$^{-1}$; measuring time 240 s),
  c. with static shear rate (130 s$^{-1}$, measuring time 180 s)
  d. with linear shear rate (130 to 0.10 s$^{-1}$; measuring time 240 s).

The viscosity is determined from the second segment (b.) of the measuring curve as function of shear rate. Measurements are performed in each case after 2 h, 24 h, 7 d and 24 d. In between measurements, the plastisols are held at 23° C.

4. The gelation behavior of plastisols is measured with a rheometer (Rheostress RS 150 (Haake GmbH) using ThermoHaake Rheowin Pro 2.96 software), using its oscillatory mode. A plate-plate system is used (plate 20 mm, gap width 0.700 mm, oscillating). The measurement comprises two segments with the following parameters:
  a. heating ramp: shear stress: 100 Pa, oscillation frequency: 1 Hz, start temperature: 30° C., end temperature: 170° C., heating rate: 10° C./min
  b. isothermal segment: temperature: 170° C., shear stress: 100 Pa, oscillation frequency: 1 Hz, measuring time: 100 s.

A sufficient amount of plastisol is applied without air bubbles to the lower plate of the measuring system. The measurement is started after applying the protective covering.

5. Tensile properties (Elastic Modulus) of compressions molded sheets—A minimum of five tensile specimens (width 12 mm) with a gauge length of 105 mm are tested in accordance to ASTM D 882 on an Instron tensile testing machine (Model 4400 R) at 50 mm/min extension rate and a load cell of 90.7 kg (200 lbs). The results are averaged to minimize variations.

6. Tensile properties (Elastic modulus) of injection molded specimens—Tensile testing of ASTM D638 type 1 test bars (overall length 165 mm, width of narrow section 13 mm, thickness 3.2 mm, length of narrow section 57 mm, width overall 19 mm, gauge length 50 mm, distance between grips 115 mm, radius of fillet 76 mm) was performed according to ASTM D 638-03 on an Instron tensile testing machine (Model 4400 R) at 50.8 mm/min extension rate and a load cell of 90.7 kg (200 lbs). Five tensile specimens were tested for each composition and the results were averaged to minimize variations.

7. Shore A hardness—the measurement is conducted according to ASTM D 2240-05. For the measurements, specimens for flexural testing (flex bars, ASTM D790; length 130 mm, width 13 mm, thickness 3.2 mm) are used. Five specimens for each plasticizer PVC compound are tested and hardness is measured at five locations for each specimen from the near gate location to the far end.

EXAMPLES

Example 1

Purification of Crude MpT

Crude MpT was obtained from a manufacturer of DMT via the Witten process. It contained 89-91 wt.-% MpT, 5.5-7 wt.-% benzoic acid methylester (BME), 0.5-2.3 wt.-% DMT, 0.1-1.5 wt.-% terephthalic aldehyde methyl ester (TAME) and traces of other compounds.

Purification by single stage distillation (at about 200° C. to 217° C., and about 1013 mbar) of MpT yielded only slightly colored MpT (20 Pt—Co units vs. 150 Pt—Co units for crude MpT) containing about 14 wt.-% BME; this material was obtained by collecting two separate fractions during the distillation. All other contaminants from the crude MpT stayed in the distillation residue.

Example 2

Synthesis of 1-butyl p-toluate

MpT, purified from crude MpT, from example 1 (1267.2 g, 8.4 mol), 1-butanol (CAS: 71-36-3, 757.4 g, 10.2 mol) and Tyzor®-TPT (630 mg) were slowly heated under nitrogen atmosphere in a 5 l glass flask equipped with a column and a distillation bridge until boiling started. The methanol resulting from the transesterification process was continuously removed and the temperature slowly rose to 215° C. In this process, slow heating was necessary because of the volatility of 1-butanol. About 280 grams of overhead (300 ml) was distilled off after reaction for 8 hours at temperatures above 175° C. The methanol overheads contained >10% 1-butanol. After cooling the mixture to room temperature, a full vacuum was applied and unreacted 1-butanol was removed. The residual 1-butanol in the plasticizer was <1%. The product contained >98% 1-butyl p-toluate with a color of 315 APHA units.

A lower color butyl-p-toluate (<20 APHA) was produced by stripping the overhead on a wiped-film evaporator at 5 mbar and 150-160° C. evaporator temperature.

Example 3

Synthesis of 1-octyl p-toluate

MpT, purified from crude MpT, from example 1 (300 g, 2 mol), 1-octanol (CAS: 111-87-5, 273 g, 2.1 mol) and Tyzor®-TPT (200 mg) were slowly heated under nitrogen atmosphere in a one l glass flask equipped with a column and a distillation bridge until boiling started. The methanol resulting from the transesterification process was continuously removed and the temperature slowly rose to 235° C. About 50 grams of methanol was removed after approximately 4 hours of reaction at 235° C. The residual MpT in the reaction mixture was about 4.3%. 1-octyl-p-toluate with a Gardner color between 3 and 6 was obtained by removing the residual MpT and 1-octanol via distillation.

Example 4

Synthesis of 2-ethylhexyl p-toluate

MpT, purified from crude MpT, from example 1 (1050.2 g, 7 mol), 2-ethylhexanol (CAS: 107-76-7; 1041 g, 8 mol) and Tyzor®-TPT (700 mg) were slowly heated under nitrogen atmosphere in a 5 l glass flask equipped with a column and a distillation bridge until boiling started. The methanol resulting from the transesterification was continuously removed and the temperature was subsequently further risen to 235° C. until about 200 grams of methanol had been distilled off (after approx. 6 hours at temperatures >175° C.). After cooling of the mixture to room temperature vacuum was applied and unreacted MpT and 2-ethylhexanol were distilled off (column head temperature up to 105° C. at 37 mmHg) until residual MpT and 2-ethylhexanol were <0.5 and <0.25%, respectively. The resulting mixture was filtered using filtering aid. The product contained >98% 2-ethylhexyl p-toluate. This product was further purified by processing through a wiped-film evaporator at 0.5 mbar at 160° C. to obtain a product with a color of <20 AHPA units.

Example 5

Synthesis of Isononyl p-toluate

MpT, purified from crude MpT, from example 1 (450 g, 3 mol), isononyl alcohol (CAS: 68526-84-1; 432 g, 3 mol) and zinc acetate dihydrate (234 mg, 1 mmol) were slowly heated under nitrogen atmosphere in a 2 l glass flask equipped with a column and a distillation bridge until boiling started. The methanol resulting from the transesterification was continuously removed and the temperature was subsequently further risen to 260° C. until the equivalent amount of methanol (122 ml) had been distilled off (after approx. 4 h). After cooling of the mixture to room temperature vacuum was applied and unreacted MpT and isononyl alcohol were distilled off (column head temperature 45-51° C. at 0.21 mbar). The temperature was increased and after separation of an intermediate fraction of residual impurities (column head temperature 55-125° C. at 0.21-0.24 mbar) the final product was distilled at 127-148° C. at 0.21-0.24 mbar. 657 g of a clear colorless (20 Pt—Co units) liquid was obtained. The product (isononyl p-toluate) contained 14% by weight isononyl benzoate as a by-product (% by weight are based on the total weight of toluate and benzoate).

Example 6

Synthesis of Isoundecyl p-toluate

MpT, purified from crude MpT, from example 1 (450 g, 3 mol), isoundecyl alcohol (CAS: 68551-08-6; 465 g, 2.7 mol) and zinc acetate dihydrate (234 mg, 1 mmol) were slowly heated under nitrogen atmosphere in a 2 l glass flask equipped with a column and a distillation bridge until boiling started. The methanol resulting from the transesterification was continuously removed and the temperature was subsequently further risen to 260° C. until the equivalent amount of methanol (122 ml) had been distilled off (after approx. 4 h). After cooling of the mixture to room temperature vacuum was applied and unreacted MpT and isoundecyl alcohol were distilled off (column head temperature 38-44° C. at 0.43-0.45 mbar). The temperature was increased and after separation of an intermediate fraction of residual impurities (column head temperature 45-98° C. at 0.3 mbar) the final product was distilled at 132-155° C. at 0.3 mbar. 639 g of a clear colorless (20 Pt—Co units) liquid was obtained. The product (isoundecyl p-toluate) contained 14% by weight isoundecyl benzoate as a by-product (% by weight are based on the total weight of toluate and benzoate).

Example 7

Synthesis of 2-Ethylhexyl p-toluate

MpT, purified from crude MpT, from example 1 (475 g, 3.2 mol), 2-ethylhexanol (CAS: 104-76-7; 412 g, 3.2 mol) and zinc acetate dihydrate (247 mg, 1.1 mmol) were slowly heated under nitrogen atmosphere in a 2 l glass flask equipped with a column and a distillation bridge until boiling started. The methanol resulting from the transesterification was continuously removed and the temperature was subsequently further risen to 220° C. until the equivalent amount of methanol (128 ml) had been distilled off (after approx. 3.5 h). After cooling of the mixture to room temperature vacuum was applied and unreacted MpT and 2-ethylhexanol were distilled off (column head temperature 56-58° C. at 0.3 mbar). The temperature was increased and after separation of an intermediate fraction of residual impurities (column head temperature 60-90° C. at 0.35 mbar) the final product was distilled at 110-130° C. at 0.4 mbar. 622 g of a clear colorless (Pt—Co units 20) liquid was obtained. The product (2-ethylhexyl p-toluate) contained 14% by weight of 2-ethylhexyl benzoate as a by-product (% by weight are based on the total weight of toluate and benzoate).

Example 8

Synthesis of Propylheptyl p-toluate

Purified MpT from example 1 (425 g, 2.8 mol), propylheptanol (commercially available from BASF; 448 g, 2.8 mol) and zinc acetate dihydrate (221 mg, 1 mmol) were slowly heated under nitrogen atmosphere in 2 liter glass flask equipped with a column and a distillation bridge until boiling started. The methanol resulting from the transesterification was continuously removed and the temperature was subsequently further risen to 260° C. until the equivalent amount of methanol (115 ml) had been distilled off (after approx. 3.5 h). After cooling of the mixture to room temperature vacuum was applied (<0.5 mbar) and unreacted MpT and propylheptanol were distilled off (column head temperature 50-56° C. at 0.26-0.27 mbar). The temperature was increased and after separation of an intermediate fraction of residual impurities (column head temperature 45-65° C. at 0.27-0.32 mbar) the final product was distilled at 137-142° C. at 0.32 mbar. 660 g of a clear colorless (20 Pt—Co units) liquid was obtained. The product (propylheptyl p-toluate) contained 13% by weight of propylheptyl benzoate as a by-product (% by weight are based on the total weight of toluate and benzoate).

Example 9

Synthesis of n-Octyl and n-Decyl p-toluate

Crude MpT (50 g, 333 mmol), Fatty Alcohol CO-1055 (available from P&G Chemicals (CAS: 68603-15-6), 39-47 wt.-% n-octanol, 51-59 wt.-% n-decanol; 45.8 g, 316 mmol) and zinc acetate dihydrate (24.8 mg, 0.11 mmol) were slowly heated under nitrogen atmosphere in a 250 ml glass flask equipped with a column and a distillation bridge until boiling started. The methanol resulting from the transesterification was continuously removed and the temperature was subsequently further risen to 260° C. until the equivalent amount of methanol (12.8 ml) had been distilled off (after approx. 3 h). After cooling of the mixture to room temperature vacuum was applied and unreacted MpT and/or alcohol were distilled off (column head temperature 45-93° C. at 0.07-0.12 mbar). The temperature was increased and after separation of an intermediate fraction of residual impurities (column head temperature 90-123° C. at 0.07 mbar) the final product was distilled at 122° C. at 0.07 mbar. 60 g of a clear colorless (20 Pt—Co units) liquid was obtained. The product (mixture of n-octyl and n-decyl p-toluate) contained 3% by weight of n-octyl and n-decyl benzoate as a by-product (% by weight are based on the total weight of toluate and benzoate).

Example 10

Synthesis of 2-Ethylhexyl p-toluate

Crude MpT (500 g, 3.3 mol), 2-ethylhexanol (CAS: 104-76-7; 412 g, 3.2 mol) and cobalt acetate tetrahydrate (282 mg, 1.1 mmol) were slowly heated under nitrogen atmosphere in a 2 l glass flask equipped with a column and a distillation bridge until boiling started. The methanol resulting from the transesterification was continuously removed and the temperature was subsequently further risen to 260° C. until the equivalent amount of methanol (128 ml) had been distilled off (after approx. 4 h). After cooling of the mixture to room temperature vacuum was applied and unreacted MpT and 2-ethylhexanol were distilled off (column head temperature 40-184° C. at 52-54 mbar). The temperature was increased and after separation of an intermediate fraction of residual impurities (column head temperature 173-213° C. at 53-55 mbar) the final product was distilled at 213-229° C. at 49-55 mbar. 639 g of a clear colorless (10 Pt—Co units) liquid was obtained. The product (2-ethylhexyl p-toluate) contained 5% by weight of 2-ethylhexyl benzoate as a by-product (% by weight are based on the total weight of toluate and benzoate).

Example 11

Synthesis of 2-Ethylhexyl p-toluate

Pure MpT (99%) from a commercial source (CAS 99-75-2, Alfa Aesar) (50 g, 0.33 mol), 2-ethylhexanol (CAS: 104-76-7; 47.7 g, 0.37 mol) and Tyzor®-TBT (193 mg, 0.57 mmol) were slowly heated under nitrogen atmosphere in a 250 ml glass flask equipped with a column and a distillation bridge until boiling started. The methanol resulting from the trans-esterification was continuously removed and the temperature was subsequently further risen to 260° C. until the equivalent amount of methanol (15 ml) had been distilled off (after approx. 3 h). After cooling a slightly beige liquid was obtained that contained 95.1% of 2-ethylhexyl p-toluate, 2.2% of methyl p-toluate and 2.4% of 2-ethylhexanol by weight. After removal of excess MpT and 2-ethylhexanol a hazy light brownish liquid was obtained that contained 99.7% of 2-ethylhexyl p-toluate by weight.

Example 12

Synthesis of 2-Ethylhexyl benzoate (Comparative)

A methyl benzoate-rich ester mixture (MB purge), similar to that described in prior art CN-A-1199042 was obtained from a manufacturer of DMT via the Witten process. 600 g of the MB purge (4.1 mol), 2-ethylhexanol (CAS: 104-76-7; 700 g, 5.4 mol) and cobalt acetate tetrahydrate (350 mg, 1.4 mmol) were slowly heated under nitrogen atmosphere in a 2 l glass flask equipped with a column and a distillation bridge until boiling started. The methanol resulting from the trans-esterification was continuously removed and the temperature was subsequently further risen to 260° C. until the equivalent amount of methanol had been distilled off (after approx. 4 h). After cooling of the mixture to room temperature vacuum was applied and unreacted MpT and 2-ethylhexanol were distilled off (column head temperature 55-125° C. at 0.7 mbar). The temperature was increased and the final product was distilled at 126° C. at 0.7 mbar. 730 g of a clear almost colorless (30 Pt—Co units) liquid was obtained. The product (2-ethylhexyl benzoate) contained 11% by weight of 2-ethylhexyl p-toluate as a by-product (% by weight are based on the total weight of toluate and benzoate).

Example 13

Determination of the Volatility

The volatility of the products was determined according to the standard ASTM D 2298-97 at 105° C. The mass losses were determined after 4 and 24 hours. The relative mass loss, compared to the mass loss of 2-ethylhexyl benzoate, is set forth in table 1.

TABLE 1

| Mass loss | mass loss 2-ethylhexyl benzoate | |
|---|---|---|
| | 4 h | 24 h |
| Ethylhexyl p-toluate | 35% | 41% |
| Isononyl p-toluate | 59% | 32% |
| Propylheptyl p-toluate | 36% | 57% |

The alkyl p-toluates of the present invention show a lower volatility than the alkyl benzoates.

Example 14

Plasticizer Viscosity

Viscosities of plasticizers di-2-ethylhexyl phthalate (DEHP, CAS: 117-81-7), di-isononyl phthalate (DINP, CAS: 68515-48-0), butyl benzyl phthalate (BBP, CAS: 85-68-7), dibutyl phthalate (DBP, CAS: 84-74-2) and dipropylenglycol dibenzoate (80%; DPGB, CAS: 27138-31-4) were determined. Due to the Newtonian behavior of the plasticizers their viscosity is independent of shear rate, the results are set forth in Table 2.

TABLE 2

| Plasticizer | Plasticizer viscosity, mPa · s |
|---|---|
| 2-ethylhexyl p-toluate | 7.6 |
| DEHP | 67 |
| DINP | 76 |
| BBP | 55 |
| DBP | 14 |
| DPGB (80%) | 140 |

The viscosity of 2-ethylhexyl p-toluate is smaller by a factor of approximately 2 to 20 compared to other plasticizers employed for PVC.

Example 15

Plastisol Preparation

The compositions of the prepared plastisols are given in Table 3. The PVC used was Vinnolit E70TT (VinnoliGmbH & Co. KG, Germany) and the stabilizer was Baerostab CT 9183 X (Baerlocher GmbH, Germany). The components were weighed in a 500 ml dissolver beaker and premixed with a spatula. The beaker was then clamped into the dissolver stirrer (Dispermat V05, Götzmann GmbH) and closed. Under isothermal conditions (23° C.) the plastisol was formulated under pulsed vacuum (95 to 115 mbar) until a homogenous plastisol was obtained, indicated by a constant torque. The plastisols were then stored at 20° C.

TABLE 3

(all amounts in phr (= parts per 100 parts PVC))

| | Formulation | | | | |
|---|---|---|---|---|---|
| | P1 | P2 | P3 | P4 | P5 |
| PVC | 100 | 100 | 100 | 100 | 100 |
| Stabilizer | 3 | 3 | 3 | 3 | 3 |
| 2-ethylhexyl p-toluate | 75 | | | | |
| DEHP | | 75 | | | |
| DINP | | | 75 | | |
| BBP | | | | 75 | |
| DBP | | | | | 75 |

Example 16

Plastisol Viscosity

Viscosities of plastisols prepared in example 15 were measured. The viscosity at shear rates of 10 $s^{-1}$ and 100 $s^{-1}$ were measured, after storage of the plastisols for 2 h, 24 h, and 7 d and the results set forth in Tables 4 (10 $s^{-1}$) and 5 (100 $s^{-1}$).

TABLE 4

| | Viscosity, mPa · s | | | | |
|---|---|---|---|---|---|
| Composition | P1 | P2 | P3 | P4 | P5 |
| 2 h | 290 | 2200 | 2800 | 2000 | 1200 |
| 24 h | 320 | 2400 | 2600 | 2300 | 2200 |
| 7 d | 350 | 2600 | 2600 | 2700 | 5700 |
| Relative increase (7 d/2 h) | 1.2 | 1.2 | 0.90 | 1.4 | 4.8 |

TABLE 5

| | Viscosity, mPa · s | | | | |
|---|---|---|---|---|---|
| Composition | P1 | P2 | P3 | P4 | P5 |
| 2 h | 220 | 2200 | 2500 | 2300 | 1100 |
| 24 h | 220 | 2300 | 2400 | 2800 | 2100 |
| 7 d | 280 | 2600 | 2600 | 3300 | 4400 |
| Relative increase (7 d/2 h) | 1.3 | 1.2 | 1.0 | 1.4 | 4 |

The lowest viscosity was found for the plastisol P1 prepared from 2-ethylhexyl p-toluate. Plastisol P1 shows good stability upon aging as indicated by the relative increase in viscosity which is comparable to plastisol P2 prepared from DEHP and slightly superior to plastisol P4 prepared from BBP. Plastisol P5 prepared from DBP shows significant increase in viscosity by a factor of more than 4.

Example 17

Gelation Behavior of Plastisols

The gelation behavior, and complex viscosity $\eta^*$, of the plastisols prepared in example 15 was measured as a function of time. A sudden strong increase of the complex viscosity indicates the onset of gelation. The lower the onset temperature the higher is the gelling efficiency. The gel point is defined as the temperature where the loss factor tan δ (tan δ=G"/G'; ratio of loss modulus G" and storage modulus G') reaches a maximum. The measured gel points are set forth in Table 6.

TABLE 6

| Composition | P1 | P2 | P3 |
|---|---|---|---|
| Gel point, ° C. | 72.5 | 84.5 | 90.2 |

The complex viscosities $\eta^*$ of the plastisols P1, P2 and P3 measurements are set forth in Table 7.

TABLE 7

| | Complex Viscosity $\eta^*$, PA · s | | |
|---|---|---|---|
| Composition | P1 | P2 | P3 |
| 50° C. | 12 | 12 | 12 |
| 60° C. | 12 | 12 | 12 |
| 70° C. | 15 | 12 | 12 |
| 75° C. | 500 | 12 | 12 |
| 80° C. | 5,000 | 14 | 12 |
| 85° C. | 9,100 | 100 | 13 |
| 90° C. | 13,000 | 1,300 | 40 |
| 95° C. | 17,500 | 3,300 | 120 |
| 100° C. | 21,500 | 5,250 | 600 |
| 105° C. | 25,000 | 7,470 | 1,550 |
| 110° C. | 26,700 | 10,100 | 3,000 |
| 115° C. | 27,200 | 13,300 | 5,200 |
| 120° C. | 24,900 | 16,400 | 8,800 |

The plastisol P1, prepared with the 2-ethylhexy p-toluate, shows a significantly improved gelation characteristic, as can be seen from the onset of viscosity increase at lower temperatures and a gel point of 72.5° C. which is 12° C. below that of P2 and 17.7° C. below that of P3, both prepared from phthalate plasticizers.

When used in plastisols the allyl p-toluates according to the present invention offer beneficial properties comprising a very low plastisol viscosity, a good plastisol stability and low gelation temperature.

Example 18

Elastic Modulus of Compression Molded PVC-plasticizer Compounds

PVC with 3 wt-% heat stabilizer (Ca—Zn stearate) was heated in individual cups to a temperature of 82° C. Varying amounts of the allyl p-toluates were added to each cup and individually mixed and sheared (iKa rw16 basic laboratory mixer) to enhance mixing and plasticizer absorption to give a uniform blend of PVC and plasticizer. The blends of PVC and plasticizer were compression molded in a 0.5 mm steel mold at 185° C. and 3 MPa pressure with a preheat time of 2 min and compression time of 3 min providing uniform sheets with dimensions of 150 mm×150 mm. The test specimens were cut into strips (width 12 mm) using a Thwing-Albert JDC Precision sample cutter and measured at 5 different locations along the gauge length to obtain an average thickness value. The elastic modulus of the various plasticized PVC sheets was measured and the results set forth in table 8.

TABLE 8

| Composition | | Elastic modulus, MPa | | | | |
|---|---|---|---|---|---|---|
| Weight-% | phr | DEHP | Isononyl p-toluate, | Isoundecyl p-toluate, | 2-ethylhexyl p-toluate, | Propylheptyl p-toluate, |
| 10 | 11 | 1978 | 1629 | 2274 | 2061 | 2138 |
| 25 | 33 | 113.3 | 27.3 | 59.6 | 23.8 | 34.0 |
| 40 | 67 | 8.0 | 6.3 | 7.6 | 8.6 | 7.5 |

Results in Table 8 demonstrate the better plasticization efficiency of the alkyl p-toluate plasticizers as compared to DEHP.

Example 19

Mechanical Properties of Injection Molded PVC-plasticizer Compounds

Dry blends with compositions given in table 9 were prepared in an industrial Herschel high speed mixer. PVC together with stearic acid, stabilizer and calcium stearate was sheared at a speed of 30 rpm up to a temperature of 82.2° C. The speed was then reduced to 18 rpm and the plasticizer along with epoxidized linseed oil was added. Shearing was continued till a temperature of 101.7° C. was reached. After cooling with the water cooling jacket to a temperature of 71.8° C. the mixture was discharged and then cooled to room temperature. The PVC dry blends were conditioned for 48 h prior to further use.

The plasticizers di-2-ethylhexyl phthalate (DEHP, CAS: 117-81-7), di-isononyl phthalate (DINP, CAS: 68515-48-0), DINCH and DOTP were used as reference plasticizers.

TABLE 9

(all amounts in phr (= parts per 100 parts PVC))

| Composition | D1 | D2 | D3 | D4 | D5 | D6 |
|---|---|---|---|---|---|---|
| PVC (Shintech SE 13300F) | 100 | 100 | 100 | 100 | 100 | 100 |
| Stabilizer (Akcros LT2001M) | 8 | 8 | 8 | 8 | 8 | 8 |
| Linseed oil (Chemtura Drapex 10.4 ELO) | 8 | 8 | 8 | 8 | 8 | 8 |
| Calcium stearate (Fisher) | 1 | 1 | 1 | 1 | 1 | 1 |
| Stearic acid 95% (Aldrich) | 5 | 5 | 5 | 5 | 5 | 5 |
| 2-ethylhexyl p-toluate | 50 | | | | | |
| DEHP | | 50 | | | | |
| DINP | | | 50 | | | |
| DINCH | | | | 50 | | |
| DOTP | | | | | 50 | |
| 2-ethylhexyl benzoate | | | | | | 50 |

ASTM tensile (ASTM D 638 type 1) and flexural specimens (ASTM D790) were prepared by injection molding (Roboshot s2000i-B-55 all electric injection molding machine). Molding parameters are given in table 10. The specimens were conditioned for 48 h at 22.8° C. and 50% relative humidity prior to use.

TABLE 10

| Injection molding parameters | |
|---|---|
| Parameter | Value |
| Shot size | 5.588 cm |
| Injection velocity | 11.43 cm/s |
| Transfer by position | 0.6 |
| Packing pressure | 414 bar |
| Packing time | 5 s |
| Extruder rpm | 200 |
| Back pressure | 10 bar |
| Decompression velocity | 2.54 cm/s |
| Cooling time | 10 s |
| Mold temperature | 40.6° C. |

Tensile testing was conducted according to ASTM D 638-03 on an Instron tensile testing machine (Model 4400 R) at 50.8 mm/min extension rate and a load cell of 90.7 kg (200 lbs). Five tensile specimens were tested for each composition and the results were averaged. Shore A hardness measurements were performed according to ASTM D 2240-05. using test bars for flexural testing (ASTM D790, flex bars). Five specimens for each plasticizer PVC compound were tested, and hardness was measured at five locations for each specimen from the near gate location to the far end. Shore A hardness values are given in Table 10. The tensile properties and hardness results are set forth in Table 11.

TABLE 11

| | Composition | | | | | |
|---|---|---|---|---|---|---|
| Property | D1 | D2 | D3 | D4 | D5 | D6 |
| Elastic modulus, MPa | 3.05 | 4.64 | 8.26 | 8.92 | 6.49 | 3.08 |
| Tensile strain at Break, % | 644 | 642 | 627 | 561 | 521 | 644 |
| Tensile stress at Break, MPa | 9.30 | 12.8 | 11.32 | 11.09 | 11.14 | 9.44 |
| Maximum load, N | 372 | 518 | 493 | 560 | 520 | 376 |
| Extension at break, mm | 322 | 322 | 313 | 280 | 261 | 322 |
| Shore A hardness | 73 | 80 | 84 | 85 | 83 | 75 |

Tensile testing specimens, prepared from the dry blends D1 and D6, were aged at 80° C. in a ventilated furnace for 24 h and 48 h. The elastic modulus of the aged specimens was measured. The relative elastic modulus of aged samples prepared from dry blend D6, normalized against the elastic modulus of aged specimens prepared from dry blend D1, are set forth in Table 12.

TABLE 12

| Time, h | Elastic modulus of D6/ elastic modulus of D1 |
|---|---|
| 0 | 101% |
| 24 | 111% |
| 48 | 136% |

The allyl p-toluates of the present invention show a superior behavior with regards to permanence in flexible PVC compositions than the alkyl benzoates.

While the invention has been described in conjunction with specific embodiments thereof, it is evident that the many alternatives, modifications, and variations will be apparent to those skilled in the art in light of the foregoing description. Accordingly, the invention is intended to embrace all such alternatives, modifications and variations as fall within the spirit and scope of the claims.

What is claimed is:

1. A method for the manufacture of an alkyl p-toluate of formula I,

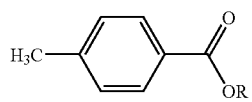

(I)

wherein R is a $C_4$-$C_{20}$ branched, linear or cyclic alkyl radical, comprising:
 oxidizing p-xylene to produce dimethyl terephthalate and a byproduct stream, wherein the byproduct stream comprises an ester comprising at least 80% by weight of $C_1$-$C_4$ alkyl p-toluic acid ester; and
 transesterifying the ester and one or more $C_4$-$C_{20}$ mono-functional branched, linear or cyclic aliphatic alcohols at a reaction temperature of 160° C. to 260° C.,
 wherein the transesterifying is in the presence of a catalyst.

2. The method according to claim 1, wherein the ester is purified prior to the transesterifying.

3. The method according to claim 2, wherein the amount of $C_1$-$C_4$ alkyl p-toluic acid ester in said ester is at least 85 weight % based on the weight of said ester.

4. The method according to claim 1, wherein the $C_1$-$C_4$ alkyl p-toluic acid ester is methyl p-toluate.

5. A method for the manufacture of an alkyl p-toluate of formula I,

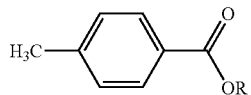

(I)

wherein R is a $C_4$-$C_{20}$ branched, linear or cyclic alkyl radical, comprising:
 a. oxidizing p-xylene to produce dimethyl terephthalate and a byproduct stream, wherein the byproduct stream comprises: an ester comprising a methyl p-toluate;
 b. transesterifying the methyl p-toluate with one or more $C_4$-$C_{20}$ mono-functional branched, linear or cyclic aliphatic alcohol in the presence of a catalyst at a reaction temperature of 160° C. to 260° C. to form a resultant product,
 c. distilling the resultant product under vacuum to remove the unreacted methyl p-toluate and alcohol,
 d. optionally raising the temperature,
 e. optionally reducing the pressure, and
 f. distilling off the alkyl p-toluate.

6. A method for the manufacture of an alkyl p-toluate of formula I,

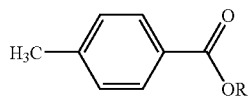

(I)

wherein R is a $C_4$-$C_{20}$ branched, linear or cyclic alkyl radical, comprising:
 a. oxidizing p-xylene to produce dimethyl terephthalate and a byproduct stream, wherein the byproduct stream comprises: an ester comprising a methyl p-toluate;
 b. transesterifying the methyl p-toluate with one or more $C_4$-$C_{20}$ mono-functional branched, linear or cyclic aliphatic alcohol in the presence of a catalyst at a reaction temperature of 160° C. to 260° C. to form a resultant product,
 c. distilling the resultant product under vacuum to remove the unreacted methyl p-toluate and alcohol to form a purified alkyl p-toluate,
 d. filtering the purified alkyl p-toluate, and
 e. optionally distilling the purified alkyl p-toluate under vacuum to distill off the alkyl p-toluate.

7. The method according to any one of claim 5, or 6, wherein the alkyl p-toluate has a color value of less than or equal to about 20 Pt—Co units.

8. The method according to claim 1, wherein the manufactured alkyl p-toluate has an AHPA color number of less than 50 Pt—Co units.

9. The method according to claim 1, wherein the transesterification is carried out without a solvent.

10. The method according to claim 1, further comprising passing the transesterified material through a wiped-film evaporator.

* * * * *